United States Patent [19]

Wingrave

[11] 4,271,698
[45] Jun. 9, 1981

[54] APPARATUS TO MEASURE PLASTICIZER ABSORPTION IN POLYMER POWDERS

[75] Inventor: James A. Wingrave, Ponca City, Okla.

[73] Assignee: Conoco, Inc., Ponca City, Okla.

[21] Appl. No.: 88,988

[22] Filed: Oct. 29, 1979

[51] Int. Cl.³ .............................................. G01N 5/02
[52] U.S. Cl. ........................................................ 73/74
[58] Field of Search ................... 73/73, 74, 76, 432 R; 177/253; 141/331

[56] References Cited

U.S. PATENT DOCUMENTS

| | | | |
|---|---|---|---|
| 1,989,003 | 1/1935 | Dunagah | 73/74 |
| 2,679,159 | 5/1954 | Messer | 73/74 |
| 2,933,110 | 4/1960 | Sharp | 141/331 |

*Primary Examiner*—S. Clement Swisher
*Attorney, Agent, or Firm*—Cortlan R. Schupbach, Jr.

[57] ABSTRACT

The invention discloses an apparatus for measuring the diffusion of liquid into solids comprising
 (a) an upper portion having substantially sloped walls, the lower end of said sloped walls meeting to form an aperture,
 (b) solids retaining means positioned at said aperture, said means being permeable to a liquid whose absorption is being measured,
 (c) a lower portion substantially cylindrical in configuration, said lower portion connected with said upper portion wherein said aperture is common to both, and wherein
 (d) both upper and lower portions are operably connected to a gravimetric scale, such that the total weight of the upper and lower portions, solids retaining means, solid content, and liquid can be weighed.

The apparatus and method taught provide an efficient easy way for measuring fusion of liquid in the solids.

10 Claims, 4 Drawing Figures

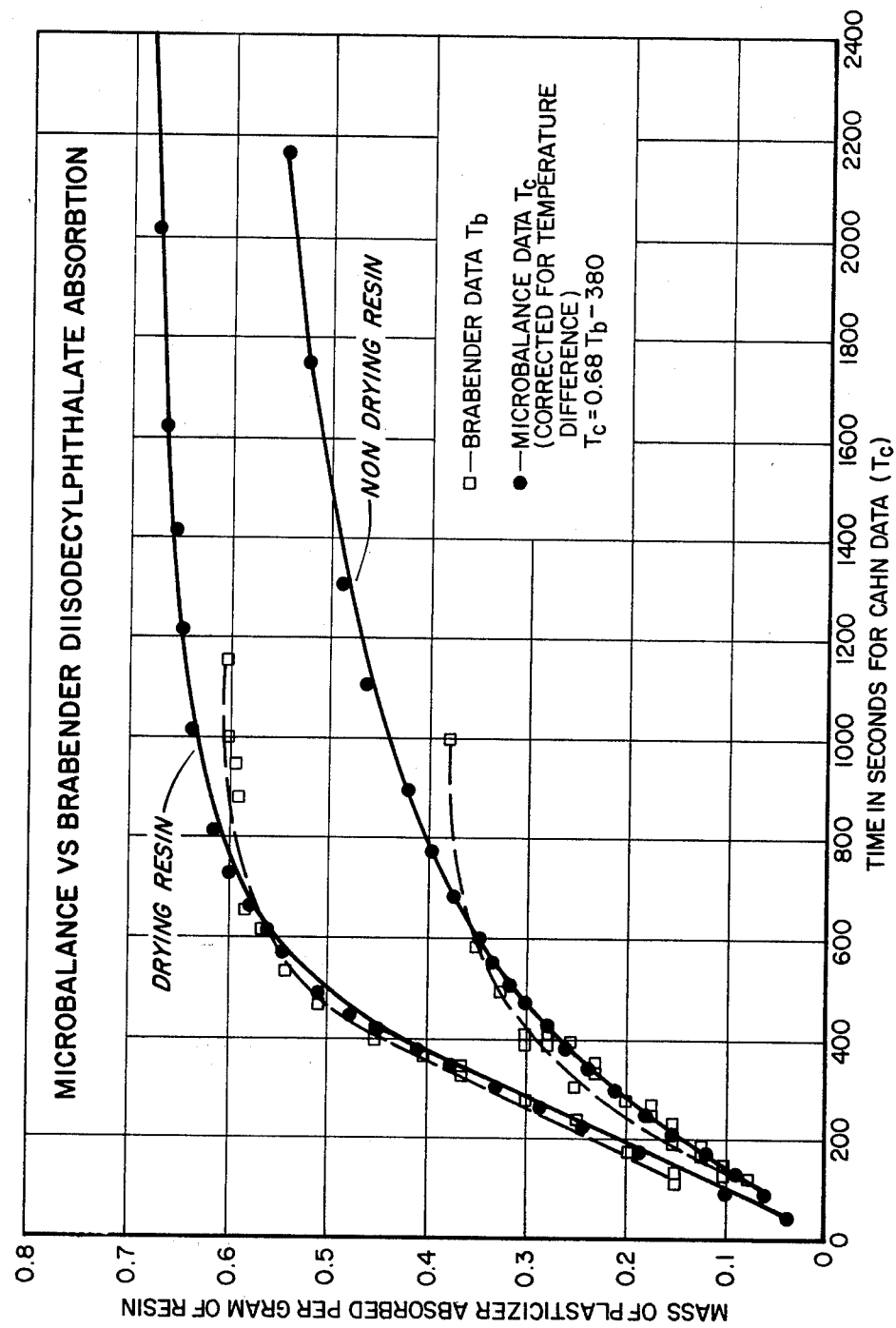

APPARATUS TO MEASURE PLASTICIZER ABSORPTION IN POLYMER POWDERS

This invention relates to a method for measuring the diffusion of liquids into solids. More particularly, this invention relates to a method and apparatus for measuring the diffusion of liquid into solids by allowing liquid to fill the interstices of solids, weighing the apparatus contents at this point, and then measuring the gradual weight increase as more liquid is diffused into the solid particles themselves.

The general field of diffusion of liquids into solids has long been of commerical interest in industry. Although primary applications with such tests are found in the plastics industry, other industries also have tests for diffusion of liquids into solids. For example, in the coal industry, water and hydrocarbon diffusion into solid particles of coal is a valuable datum. In the wood industry, the diffusion of water, hydrocarbons and paints into wood pores is necessary to know the effect of various treatments. In the widespread and growing plastics and rubber industries, the diffusion of toluene, other aromatics, aldehydes, ketones, water and various plasticizers into rubber, polystyrene, polyethylene, polyvinyl chloride, and other plastics must be known. These plasticizers and antioxidants provide valuable protection to finished products and allow processing to proceed more easily and at much less energy costs. Thus the effect of any given liquid product on the solid resin or polymer particles is a valuable datum.

Currently, the instrument by which plasticizer absorption is made currently measured throughout the plastics and rubber industry is the Brabender Plasticorder. However, this instrument is a complex mechanical device which measures torque required to mix the plasticizer with polymer or plastic powder and provides results which must be interpreted in order to deduce the plasticization behavior of the plastic or polymer powder. These instruments can be obtained from the Brabender Corporation. Standard Brabender plasticizer tests are well known in the art. A description of the procedure used can be found at AST, D2396-69, Powder-Mix Test of Poly(Vinyl Chloride) Resins Using a Torque Rheometer ASTM Standards Part 26.

However, this widely used instrument has many drawbacks. For example, only one quantity of plasticizer can be determined from one Brabender experiment. Instantaneous plasticizer absorption rates cannot be determined using only one experiment; instead several experiments over a range must be carried out. In addition, the Brabender plasti-corder uses about 100 milligrams of powder in order to provide interpretable results. Finally, the results must be interpreted by one skilled in carrying out the experiment in order to give reliable results reproduceable within a given acceptable margin of error. The same tests carried out by different operators can vary significantly in results.

It would therefore be of great benefit to provide a method for direct determination of liquid absorption in the solid which requires no interpretive results.

It is therefore an object of the present invention to provide an improved method for determining the diffusion of liquids in the solids. Other objects will become apparent to those skilled in this art as the description proceeds.

It has now been discovered in accordance with the instant invention that improved measurement of diffusion of liquid into solids can be obtained from an apparatus comprising (a) an upper portion having substantially sloped walls, the lower end of said sloped walls meeting to form an aperature, (b) solids retaining means positioned at said aperature, said means being permeable to a liquid whose absorption is being measured, (c) a lower portion substantially cylindrical in configuration, said lower portion connected with said upper portion wherein said aperature is common to both, and wherein (d) both upper and lower portions are operably connected to a gravimetric scale, such that the total weight of the upper and lower portions, solids retaining means, solid, content, and liquid can be weighed.

The instant invention has major advantages over the prior art apparatus. Using the instant invention, the time required for any desired quantity of liquid absorption can be determined directly from a single experiment as opposed to limited data available from Brabender experiments. In addition, the rate of plasticizer absorption at any given time and the absorbed amount can be determined from a single experiment. The instant invention method requires much less solid than the prior art method and requires no interpretation of results. No mechanical losses due to friction or machine wear are encountered.

The invention is more concretely described with reference to the figures and experiments set forth below wherein all parts and percentages are by weight unless otherwise specified. The figures and experiments are provided to illustrate the instant invention and not to limit it.

BRIEF DESCRIPTION OF THE DRAWINGS

FIG. 4 is a comparison of the instant invention as opposed to prior art Brabender absorption using polyvinyl chloride resin and diisodecylphthalate. cl DETAILED DESCRIPTION OF THE DRAWINGS FIG. 1 shows the use of a Cahn microbalance plasticizer absorption apparatus used to determine the rate of diisodecylphthalate plasticizer into polyvinyl chloride resin. The Cahn microbalance is produced and sold by Cahn Instruments. In the apparatus used, the microbalance was connected to the resin flask described in FIG. 2, said resin flask containing a glass wool plug and about 100 mg of polyvinyl chloride resin. Plasticizer bulb was filled with 50 ml of the desired plasticizer (diisodecylphthalate) and attached to the balance chamber with a 90° stainless steel tubing elbow using Teflon ferrels. The plasticizer was cryogenically degassed. The balance chamber containing the resin flask and resin was then evacuated to prevent air from interfering with plasticizer contact with the resin particles. The plasticizer bulb and evacuated balance chamber were then thermostated in an oil bath at 80°±0.25° C. for 1 hour. After thermoequilibrium was achieved, the plasticizer flask was inverted so that plasticizer could flow into the balance chamber until it reached the apex of the conical section of the resin flask. Plasticizer then wicked up the lower tube of the resin flask by capillary force and rapidly filled the resin, interstices and intraparticle pores and voids in about 1 minute. Since the resin and plasticizer were initially evacuated, the plasticizer did not trap air in the pores and as a result, the plasticizer filled such pores hydrostatically full.

After pore filling, the diffusion of the plasticizer into the solid PVC resin occurred over a period of 10 minutes or longer.

Figure 1:
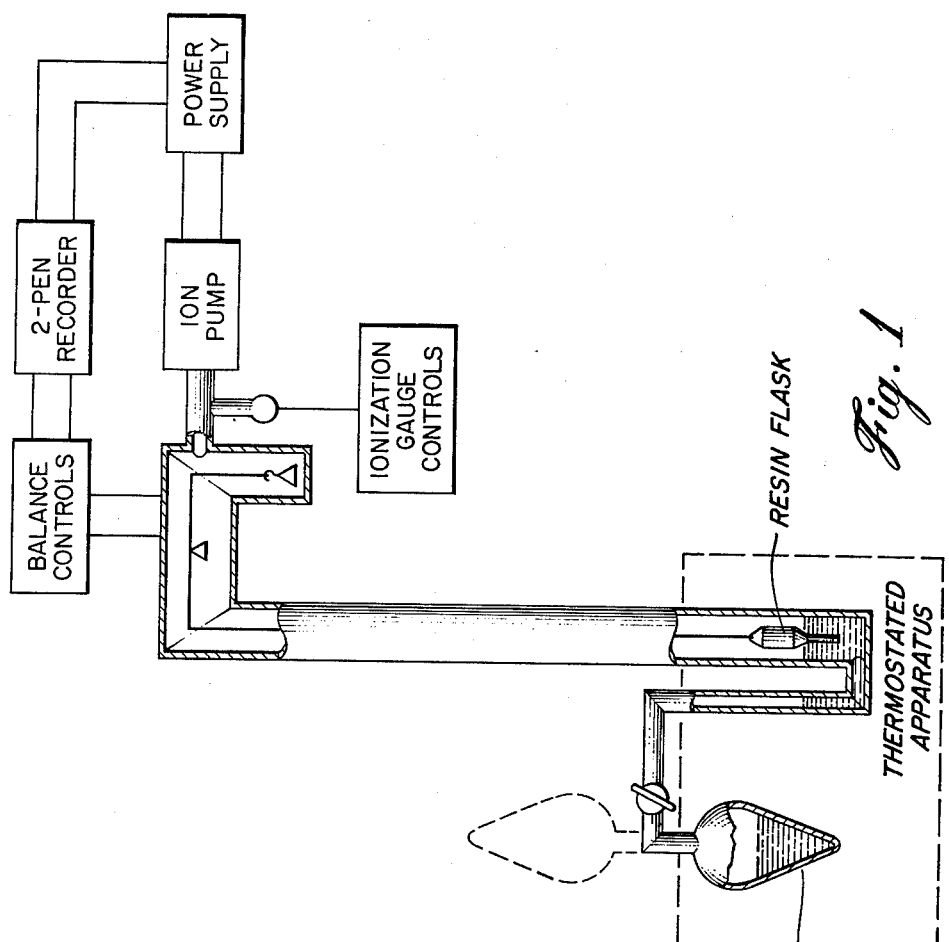
FIG. 1 is an overall schematic showing the apparatus of the instant invention.
Figure 2:
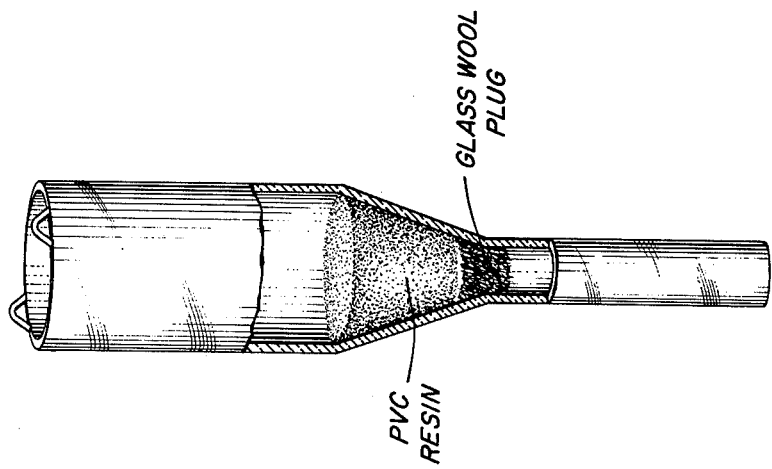
FIG. 2 is a cross-sectional view of a sample resin flask giving the noncritical diameters used in the flask actually used for the data set forth in the experiment.

FIG. 2 shows the resin flask used in the experiments. The resin flask is made from 12 mm outside diameter tubing (10 mm inside diameter) which was drawn to a 3 mm outside diameter (1.75 mm inside diameter) lower tube. Both the upper and lower portions were approximately 20 mm in length with the sloping portion being about 10 mm in length. The aperature between the upper and lower portions was plugged with glass wool and about 100 mg of PVC resin was inserted therein. The entire loaded resin flask was then suspended from a Cahn microbalance.

Figure 3:
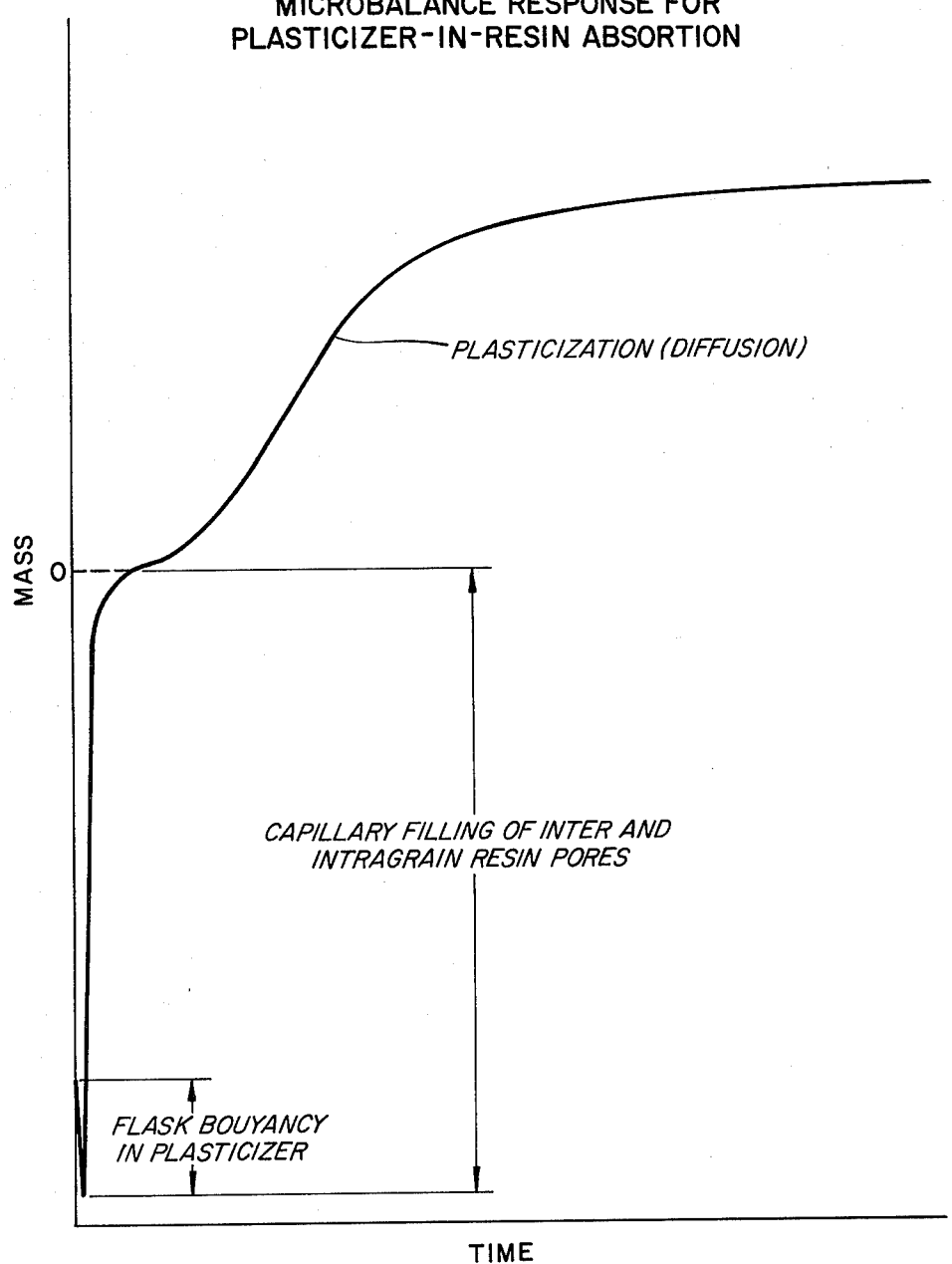
FIG. 3 is a typical fusion chart obtained using the apparatus of the instant invention.

FIG. 3 shows a typical response for plasticizer and resin absorption for the diisodecylphthalate plasticizer used. In the sample shown in FIG. 3, an initial drop is seen by the flask bouyancy in the plasticizer, which is rapidly overcome by the capillary filling of the intergrain and intragrain resin pores. Once this filling has been accomplished, the recorder is zeroed and plasticizer diffusion is measured over a given length of time until the curve levels out.

FIG. 4 is comparative date of the technique of the instant invention versus Brabender absorption for the same PVC resin and the same plasticizer. The formula $T_C = 0.68\ T_b - 380$ is an emperical expression of the relationship between the two after correction for temperature difference, since the Brabender test is normally carried out at about 90° C. The excellent correlation between the two is readily apparent in the figure.

Thus the instant invention also comprises a method for measuring diffusion of liquid into solids, said method using an apparatus having
(a) an upper portion having substantially sloped walls, the lower end of said sloped walls meeting to form an aperature,
(b) solids retaining means positioned at said aperature, said means being permeable to a liquid whose absorption is being measured,
(c) a lower portion substantially cylindrical in configuration, said lower portion connected with said upper portion wherein said aperature is common to both, and wherein
(d) both upper and lower portions are operably connected to a gravimetric scale, such that the total weight of the upper and lower portions, solids retaining means, solid content, and liquid can be weighed, said method comprising
(e) placing a solid into the upper portion of said apparatus, said solid retained by said retaining means,
(f) placing liquid whose diffusion is to be measured around the lower portion of said apparatus, allowing capillary forces to draw said fluid around said solid,
(g) weighing the entire apparatus, solid and liquid to obtain a first weight,
(h) waiting a sufficient length of time, then
(i) then recording a second weight of the entire apparatus liquid and solid, and
(j) determining the difference between the first and second weights to obtain the weight of liquid diffused into solid.

In addition, the instant invention allows the recording of the rate of absorption by simple measurement of the time and temperature necessary for the graph to come to weight equilibrium.

In the apparatus actually built and tested, the resin flask had about a 12 ml outside diameter proportion and a 3 ml outside diameter lower portion, each portion comprising about 20 mm in length. However, the diameter and dimensions of the resin flask are not critical and can be varied, dependent upon the solid and liquid whose diffusion properties are being measured. For example, in coal or wood a much larger flask would be appropriate. The dimensions of the flask are not critical.

Solids retaining means at the aperature between the upper and lower portions of the resin flask are not critical other than that it does not absorb the liquid whose diffusion is being measured. Representative examples of suitable materials are fiberglass, glass wool, steel wool, glass beads, glass screens and metal screens.

Dependent upon the liquid and solid whose diffusion is being measured, it may be desirable to carry out the liquid diffusion tests under at least a partial vacuum. However, this is not critical and may vary from test to test. For example, in measuring the diffusion of paint into wood particles to simulate actual operating conditions, no vacuum would be used. In addition, the use of vacuum depends somewhat upon the size of the solid particles, since air is more easily trapped in finally divided solids. Large solids such as wood chips or coal would not normally require a vacuum while finer solids such as PVC resins are more conveniently tested under at least a partial vacuum.

The balance used can be any balance which gives an accurate determination of the weight increase. For this purpose, the electronic balances such as the Cahn balance or Mettler balance are more convenient, especially when connected to a recorder to graphically demonstrate the increase in weight. Such balances also require much less operator attention in addition to being much more accurate.

If a vacuum apparatus is to be used with a particular liquid and solid being tested, then a balance designed for operation in a vacuum such as the Cahn 1000 microbalance should be used.

The temperature of the experiment should be determined according to the solid and liquid whose diffusion is being measured. For example, a very slow diffusion rate could be increased by raising the temperature, whereas a very fast diffusion rate could be slowed for experimental purposes by lowering the temperature. Particle size, temperature, and pressure are all variables dependent upon the liquid and solid whose absorption is being measured. The instant method and apparatus are efficient for all such materials so long as they are tested under comparable conditions, such as particle size, temperature and pressure. Such an apparatus is especially useful for quality control and experimental work where comparative results are desirable.

Experiments were carried out using the method and apparatus of the instant invention to determine the diffusion rate of diisodecylphthalate into PVC resin. In obtaining data set forth in FIG. 4, two resins rated as drying and non-drying in a diisodecylphthalate dry time test were measured for plasticizer absorption on the Cahn balance. The Brabender absorption or dry times for these materials using the same plasticizer were measured. After adjusting the time coordinate for the difference in temperatures (80° C. for Cahn balance and 88° F. for Brabender test), nearly identical results were obtained between the two methods as set forth in FIG. 4.

Thus it is clear that the method of the instant invention is a greatly improved technique for studying diffusion of liquids into solids.

The apparatus and the process of the instant invention is adaptable to any liquid solid diffusion process by simply altering the particle size of the solid, the temperature, and in some instances the atmospheric pressure. Representative examples of solids and liquid diffusants which can be tested in the apparatus and method of the instant invention are coal with liquids such as water and hydrocarbon; rubber and synthetic rubber with liquids such as toluene and other aromatic solvents; wood with water, hydrocarbons and paints; polystyrene with liquids such as aldehydes, ketones and water; polyvinyl chloride with liquids such as dioctylphthalate, diisodecylphthalate, and ditridecylphthalate; and polyethylene with liquids such as water and solvents. Many of these solid/liquid diffusions cannot be measured in a Brabender apparatus.

The apparatus and method of the instant invention measures absorption of bulk liquids whereas prior art methods are designed to measure vapor adsorption in solids also.

For example, in the tests actually carried out using polyvinyl chloride resin, the resin particle size ranged from about 50 mm to about 500 mm and the test was carried out at temperatures ranging from about 70° C. to about 100° C. The pressure ranged from 0.054 torr to less than $5.0 \times 10^{-5}$ torr. Time of the test can vary considerably depending upon the conditions used, but it is only essential that the test be continued until the increasing amount of weight absorbed stabilizes at a given point. Thus the time is variable. The tests actually carried out using PVC at the time of about ½ hour is necessary for the pressure and temperature of ranges used.

While certain embodiments and details have been shown for the purpose of illustrating this invention, it will be apparent to those skilled in this art that various changes and modifications may be made herein without departing from the spirit or scope of the invention.

I claim:

1. An apparatus for measuring the diffusion of liquid into solids comprising
    (a) an upper portion having substantially sloped walls, the lower end of said sloped walls meeting to form an aperature,
    (b) solids retaining means positioned at said aperature, said means being permeable to a liquid whose absorption is being measured,
    (c) a lower portion substantially cylindrical in configuration, said lower portions connected with said upper portion wherein said aperature is common to both, and wherein
    (d) both upper and lower portions are operably connected to a gravimetric scale, such that the total weight of the upper and lower portions, solids retaining means, solid content, and liquid can be weighed.

2. An apparatus as described in claim 1 wherein the solids retaining means is selected from the group consisting of glass wool, steel wool, fiberglass and metal screens.

3. A method for measuring diffusion of liquid into solids, said method using an apparatus having
    (a) an upper portion having substantially sloped walls, the lower end of said sloped walls meeting to form an aperature,
    (b) solids retaining means positioned at said aperature, said means being permeable to a liquid whose absorption is being measured,
    (c) a lower portion substantially cylindrical in configuration, said lower portions connected with said upper portion wherein said aperature is common to both, and wherein
    (d) both upper and lower portions are operably connected to a gravimetric scale, such that the total weight of the upper and lower portions, solids retaining means, solid content, and liquid can be weighed, said method comprising
    (e) placing a solid into the upper portion of said apparatus, said solids retained by said retaining means,
    (f) placing liquid whose diffusion is to be measured around the lower portion of said apparatus, allowing capillary forces to draw said fluid around said solid,
    (g) weighing the entire apparatus solid and liquid to obtain a first weight,
    (h) waiting a sufficient length of time,
    (i) recording a second weight of the entire apparatus liquid and solid, and
    (j) determining the difference between the first and second weights to obtain the weight of liquid diffused into solid.

4. A method as described in claim 3 wherein the solid tested is polyvinyl chloride resin.

5. A method as described in claim 4 wherein the liquid whose absorption is to be measured is a polyvinyl chloride plasticizer.

6. A method as described in claim 5 wherein the plasticizer is selected from the group consisting of dioctylphthalate, diisodecylphthalate, and ditridecylphthalate.

7. A method as described in claim 6 wherein the pressure during testing is from about $0.9 \times 10^{-5}$ torr to about 0.05 torr.

8. A method as described in claim 7 wherein the temperature ranges from about 70° C. to about 100° C.

9. A method as described in claim 3 wherein the solid tested is selected from the group consisting of rubber, natural rubber, wood, polyethylene, polypropylene, coal and polystyrene.

10. A method as described in claim 9 wherein the liquid is selected from the group consisting of hydrocarbons containing from 1 to 20 carbon atoms, aromatic hydrocarbons containing from 6 to 30 carbon atoms, water, aldehydes, and ketones.

* * * * *